US008088625B2

(12) United States Patent
Itoh

(10) Patent No.: US 8,088,625 B2
(45) Date of Patent: Jan. 3, 2012

(54) METHOD FOR DETECTION OF FAMILIAL COMBINED HYPERLIPIDEMIA

(75) Inventor: Yasuki Itoh, Niigata (JP)

(73) Assignee: Denka Seiken Co., Ltd., Tokyo (JP)

( * ) Notice: Subject to any disclaimer, the term of this patent is extended or adjusted under 35 U.S.C. 154(b) by 42 days.

(21) Appl. No.: 12/299,165

(22) PCT Filed: May 1, 2007

(86) PCT No.: PCT/JP2007/059291
§ 371 (c)(1),
(2), (4) Date: Oct. 31, 2008

(87) PCT Pub. No.: WO2007/126099
PCT Pub. Date: Nov. 8, 2007

(65) Prior Publication Data
US 2009/0317846 A1  Dec. 24, 2009

(30) Foreign Application Priority Data

May 1, 2006  (JP) ................................. 2006-127591

(51) Int. Cl.
*G01N 33/92* (2006.01)
*C12Q 1/60* (2006.01)
(52) U.S. Cl. ............ 436/71; 436/63; 436/174; 436/175; 436/177; 435/11
(58) Field of Classification Search ..................... 436/63, 436/71, 174, 175, 177; 435/11; 422/61, 422/73, 430
See application file for complete search history.

(56) References Cited

U.S. PATENT DOCUMENTS

| | | | |
|---|---|---|---|
| 6,811,994 B1 * | 11/2004 | Miyauchi et al. | 435/18 |
| 7,544,515 B2 * | 6/2009 | Itoh et al. | 436/71 |
| 2009/0263844 A1 * | 10/2009 | Itoh | 435/19 |
| 2009/0280501 A1 * | 11/2009 | Camejo et al. | 435/7.1 |
| 2010/0035288 A1 * | 2/2010 | Itoh | 435/11 |
| 2010/0041080 A1 * | 2/2010 | Aratake et al. | 435/11 |

FOREIGN PATENT DOCUMENTS

| JP | 2002-139501 | | 5/2002 |
|---|---|---|---|
| WO | 2004053500 | * | 6/2004 |

OTHER PUBLICATIONS

Veerkamp et al. Arteriosclerosis, Thrombosis & Vascular Biology, vol. 22, 2002, pp. 274-282.*
Supplementary European Search Report EP 07 74 2726 dated Jun. 24, 2009.
Tsutomu Hirano et al., "Clinical Significance of Small Dense Low-Desity Lipoprotein Cholesterol Levels Determined by the Simple Precipitation Method", Arterioscler Thromb Vasc Biol., Mar. 2004, pp. 558-563.
Amir F. Ayyobi et al., "Small, Dense LDL and Elevated Apolipoprotein B Are the Common Characteristics for the Three Major Lipid Phenotypes of Familial Combined Hyperlipidemia", Arterioscler Thromb Vasc Biol., Jul. 2003, pp. 1289-1294.
Tsutomu Hirano et al., "A novel and simple method for quantification of small dense LDL", Journal of Lipid Research vol. 44, 2003, pp. 2193-2201.
Tsutomu Hirano et al., "Measurement of Small Dense Low-density Lipoprotein Particles", Journal of Atherosclerosis and Thrombosis, vol. 12, No. 2, pp. 67-72, Jan. 1, 2005.
Nathan D. Wong et al., "Preventive cardiology a practical approach", 2004, McGraw-Hill Professional, XP002531746, pp. 114-115.
Hooman Allayee et al., "Families with Familial Combined Hyperlipidemia and Families Enriched for Coronary Artery Disease Share Genetic Determinants for the Atherogenic Lipoprotein Phenotype", Am. J. Hum. Genet. 63:577-585, 1998.
Guido Franceschini et al., "Pravastatin Effectively Lowers LDL Cholesterol in Familial Combined Hyperlipidemia Without Changing LDL Subclass Pattern", vol. 14, No. 10, Oct. 1994, pp. 1569-1575.
John E. Hokanson et al., "Plasma Triglyceride and LDL Heterogeneity in Familial Combined Hyperlipidemia", Arteriosclerosis and Thrombosis, vol. 13, No. 3, Mar. 1993, pp. 427-434.
Hidenori Arai, "Familial Combined Hyperlipidemia and Arteriosclerosis Separate Volume", Journal of Clinical and Experimental Medicine Diabetes, Metabolic Syndrome State of Arts, 2004-2006, Apr. 2004, pp. 529-531.
Yasuki Ito et al., "Small Dense LDL—New Simple Method for Small Dense LDL: Development of a New Quantification Method and Clinical Significance", Research and Development Department Denka Seiken Co., Ltd. Chuo-ku Tokyo 103-0025, pp. 406-413, 2004.

* cited by examiner

*Primary Examiner* — Maureen Wallenhorst
(74) *Attorney, Agent, or Firm* — Stephen A. Brent; Foley & Lardner LLP

(57) ABSTRACT

An object of the present invention is to provide an excellent method for detection and diagnosis of familial combined hyperlipidemia. The present invention relates to a method for detection of familial combined hyperlipidemia by measuring the concentration of small, dense LDL cholesterol in a sample collected from a subject.

7 Claims, 3 Drawing Sheets

|  | Confirmed diagnosis | | |
|---|---|---|---|
|  | + | − | |
| Present invention sdLDL>40mg/dL  + | 12 | 156 | 168 |
| − | 1 | 1176 | 1177 |
|  | 13 | 1332 | 1345 |

Sensitivity 92.3 %
Specificity 88.3 %

B

|  | Confirmed diagnosis | | |
|---|---|---|---|
|  | + | − | |
| LDL size  + | 4 | 113 | 117 |
| − | 9 | 1218 | 1227 |
|  | 13 | 1331 | 1344 |

Sensitivity 30.8 %
Specificity 91.5 %

C

|  | Confirmed diagnosis | | |
|---|---|---|---|
|  | + | − | |
| ApoB/LDL>1.0  + | 1 | 33 | 34 |
| − | 12 | 1299 | 1311 |
|  | 13 | 1332 | 1345 |

Sensitivity 7.7 %
Specificity 97.5 %

D

|  | Confirmed diagnosis | | |
|---|---|---|---|
|  | + | − | |
| ApoB/LDL >1.0 or LDL size  + | 4 | 125 | 129 |
| − | 9 | 1207 | 1216 |
|  | 13 | 1332 | 1345 |

Sensitivity 30.8 %
Specificity 90.6 %

METHOD FOR DETECTION OF FAMILIAL COMBINED HYPERLIPIDEMIA

TECHNICAL FIELD

The present invention relates to a method for detection and diagnosis of familial combined hyperlipidemia.

BACKGROUND ART

Low density lipoprotein (LDLs) plays a major role in cholesterol transport in blood and are risk factors for arteriosclerotic diseases. It is known that small, dense lipoprotein (hereinafter, referred to as "small, dense LDL"), which is particularly small in particle size among LDL and higher in specific gravity compared with standard LDL, have arteriosclerosis-inducing ability at a level several times higher than that of normal LDL.

Familial combined hyperlipidemia (hereinafter, referred to as "FCHL") is based on type IIb phenotype under WHO classification of hyperlipidemia by type. FCHL shifts to type IIa or IV because of factors such as diet. Familial hyperlipidemia does not present any specific type, so that it is defined as hereditary hyperlipidemia presenting various phenotypes including Ia, IIb, and IV. FCHL is a type of primary hyperlipidemia that tends to cause arteriosclerotic diseases. It is said that the frequency of FCHL is extremely high, impacting about one out of 100 persons and 30% or more of FCHL cases causes coronary artery diseases.

The presence of small, dense LDL in blood samples of FCHL patients has been suggested by analysis using electrophoresis (see Journal of Lipid Research 2002; 43: 598-603; Circulation 2004; 109: 2980-2985; and Research Report on Specified Diseases, Primary Hyperlipidemia, 2000, Research Division of the Ministry of Health, Labour and Welfare (2000: 37-41)). The presence of small, dense LDL is demonstrated by the fact that analysis of the electrophoretic image of a blood sample using a densitometer results in 25.5 nm or less as an LDL main peak. This suggests the quality of LDL that is microparticulated. Furthermore, in FCHL, very low density lipoprotein (VLDLs) is synthesized excessively. Hence, it has been suggested that apoprotein B is thus present excessively relative to LDL cholesterol and then the ratio of apoprotein B to LDL cholesterol increases (see Research Report on Specified Diseases, Primary hyperlipidemia, 2000, Research Division of the Ministry of Health, Labour and Welfare (2000: 37-41)). In small, dense LDL, while the content (percentage) of cholesterol in LDL particles decreases, one molecule of apoprotein B is always present in one molecule of an LDL particle. Thus, it can be said that an increased ratio of apoprotein B to LDL cholesterol indirectly indicates the presence of small, dense LDL.

However, when LDL of normal sizes other than small, dense LDs increases together with small, dense LDL, the presence of small, dense LDL cannot be precisely and specifically detected with the above method, which involves finding the quality of LDL. This may result in misdiagnosis concerning whether or not a subject disease is familial combined hyperlipidemia. Moreover, when only the measured value of apoprotein B is used, evaluation is made with the inclusion of hyper-remnant blood diseases, resulting in low detection accuracy.

DISCLOSURE OF THE INVENTION

Objects to be Attained by the Invention

An object of the present invention is to provide a good method for detection and diagnosis of familial combined hyperlipidemia.

Means for Attaining the Objects

As a result of concentrated studies, the present inventors have discovered that cholesterol levels in small, dense LDL are extremely high in samples of FCHL patients. Furthermore, LDL size measurement by conventional electrophoresis or calculation of the ratio of the measured value of apoprotein B to the same of LDL cholesterol are burdensome in terms of time and expense. However, according to the method of the present invention, FCHL detection can be simply performed.

Specifically, the present invention provides a method for detection and diagnosis of familial combined hyperlipidemia by measuring small, dense LDL cholesterol in a sample of an FCHL patient.

Furthermore, the present invention provides a method for evaluation and determination of the risk of occurrence of an event such as arteriosclerosis in FCHL and a method for evaluation and determination of whether or not arteriosclerosis in FCHL is severe.

Specifically, the present invention provides the following methods and kit.

[1] A method for detection of familial combined hyperlipidemia, comprising measuring the concentration of small, dense LDL cholesterol in a sample collected from a subject.

[2] The method for detection of familial combined hyperlipidemia according to [1], comprising measuring the concentration of small, dense LDL cholesterol in a sample collected from a patient, in which sample the TG or LDL-C level is normal.

[3] The method for detection of familial combined hyperlipidemia according to [1] or [2], in which measurement of the concentration of small, dense LDL cholesterol comprises:

a first step of separating small, dense LDL from LDL other than the small, dense LDL in a sample or eliminating cholesterol in a sample by performing reaction for LDL other than the small, dense LDL; and a second step of measuring the concentration of cholesterol in small, dense LDL after separation or elimination of the LDL other than the small, dense LDL.

[4] The method according to any one of [1] to [3], in which the sample is a serum or plasma and by which a subject is determined to be affected with familial combined hyperlipidemia when the measured concentration of small, dense LDL cholesterol in the serum or plasma is higher than 40 mg/dL.

[5] A method for determination of the risk of the occurrence of arteriosclerotic disease in a patient with familial combined hyperlipidemia, comprising measuring the concentration of small, dense LDL cholesterol in a sample collected from a subject.

[6] The method for determination of the risk of the occurrence of arteriosclerotic disease in a patient with familial combined hyperlipidemia according to [5], in which an increase in the concentration of small, dense LDL cholesterol in a sample collected from a subject indicates an increased risk of the occurrence of arteriosclerotic disease in the subject.

[7] The method for determination of the risk of the occurrence of arteriosclerotic disease in a patient with familial combined hyperlipidemia according to [5] or [6], in which the measurement of the concentration of small, dense LDL cholesterol comprises:

a first step of separating small, dense LDL from LDL other than the small, dense LDL in a sample or eliminating cholesterol in a sample by performing reaction for LDL other than the small, dense LDL; and a second step of measuring the concentration of cholesterol in the small, dense LDL after separation or elimination of the LDL other than the small, dense LDL.

[8] The method according to any one of [5] to [7], in which the sample is a serum or plasma and by which it is determined that the risk of the occurrence of arteriosclerotic disease is present in a patient with familial combined hyperlipidemia when the measured concentration of small, dense LDL cholesterol in the serum or plasma is higher than 40 mg/dL.

[9] A kit for detection of familial combined hyperlipidemia, comprising a reagent for measurement of small, dense LDL cholesterol.

EFFECT OF THE INVENTION

As in Example 1, small, dense LDL cholesterol levels in a group of FCHL patients were clearly higher than such levels in a group of healthy subjects. Furthermore, in Example 2, lipid items of samples of FCHL patients were measured. As a result, TG levels were found to be high or LDL-C levels were found to be high, suggesting that hyperlipidemia type differs depending on the individual. However, small, dense LDL cholesterol levels were always high in any cases, demonstrating that FCHL can be precisely detected by measurement of small, dense LDL cholesterol levels.

This description hereby incorporates the entire content of the description and/or the drawings of Japanese Patent Application No. 2006-127591, which is the basis of the priority claim of this application.

BRIEF DESCRIPTION OF THE DRAWINGS

FIG. 3 shows the results of comparing a method for detection of FCHL with the use of an sdLDL-C value obtained by the method of the present invention as a cut-off value (FIG. 3A), a method based on LDL sizes (FIG. 3B), a method based on the ratios of apoprotein B to LDL cholesterol (FIG. 3C), and a method based on LDL sizes or the ratios of apoprotein B to LDL cholesterol (FIG. 3D).

BEST MODES FOR CARRYING OUT THE INVENTION

Figure 1:
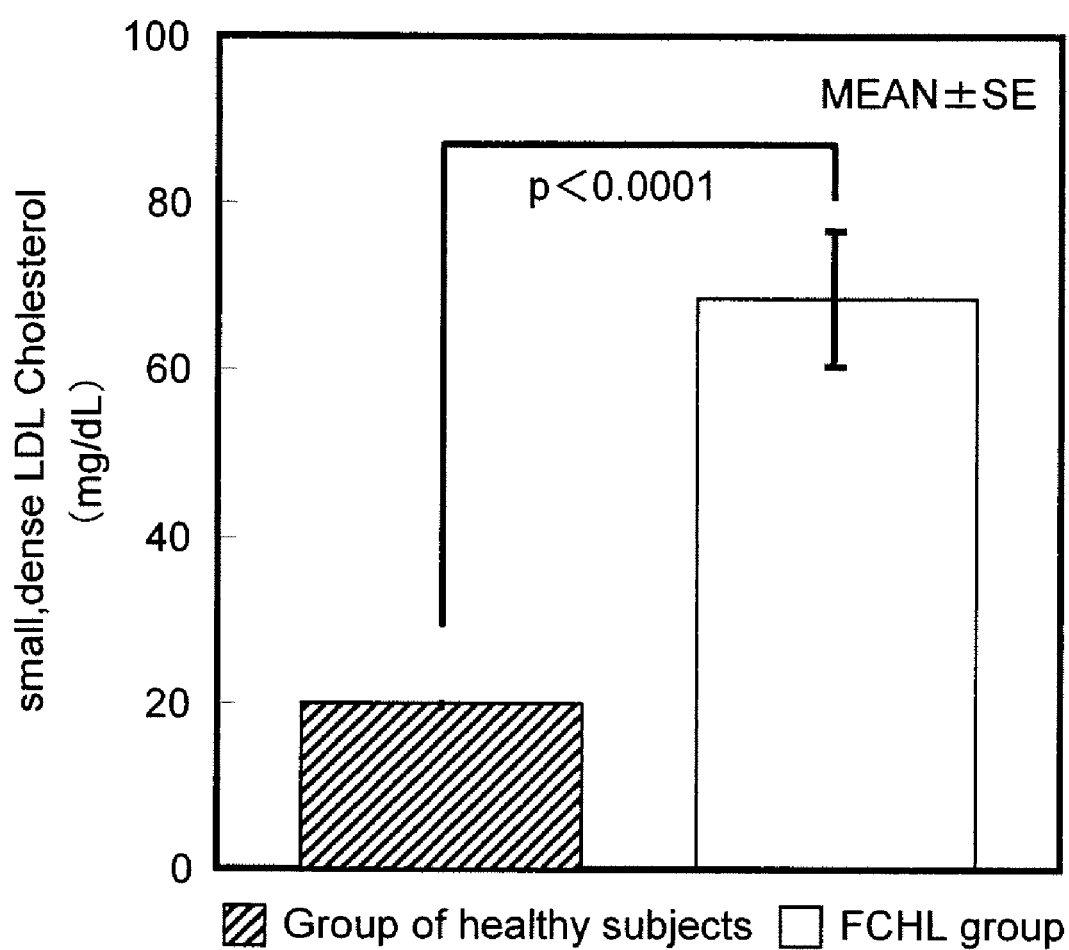
FIG. 1 shows mean small, dense LDL cholesterol levels in a group of healthy subjects and an FCHL group.

In the present invention, a serum or plasma is used as a sample.

Furthermore, in the present invention, a measured concentration of small, dense LDL cholesterol was used for detection and diagnosis to discern whether or not a subject is affected with FCHL.

Small, dense LDL is, in general, a sub-fraction of an LDL fraction, with a diameter ranging from approximately 22.0 nm to approximately 25.5 nm and specific gravity ranging from 1.040 to 1.063. The reason why LDL is sub-fractionated based on particle size is that small LDL among LDL needs to be separately measured because such LDL with small particle diameters have a high tendency of inducing arteriosclerosis such as coronary arteriosclerosis and are higher in malignancy than other LDL. The distribution of diameter and that of specific gravity of LDL are sequential. Thus, it is impossible to clearly determine that an LDL with a specific gravity at or higher than a certain level indicates a particularly high degree of malignancy. Thus the specific gravity ranging from 1.040 to 1.063 described above does not constitute an established characteristic of small, dense LDL. The specific gravity range is rather obtained by dividing another specific gravity range between 1.019 and 1.063 (widely used and established as the specific gravity of LDL) at the median point. For example, in another report, small, dense LDL is fractionated in the range between 1.044 and 1.060 (Atherosclerosis: 106 241-253 1994). The specific gravity range to be employed for small, dense LDL somewhat differs depending on researchers. In all cases, the presence of small, dense LDL is associated with clinical malignancy when fractionation is performed using such specific gravity ranges.

An older method as a method for measurement of small, dense LDL is electrophoresis. Electrophoresis is a method by which the mobility or particle diameter of LDL is measured using polyacrylamide gel. However, with electrophoresis, the presence of small, dense LDL can be confirmed, but specific ingredients are not quantified (JAMA, 260, p. 1917-21, 1988, Arteriosclerosis, 25, p. 67-70, 1997). Moreover, another older method is a method that involves measuring the number of LDL particles using NMR (Handbook of lipoprotein Testing, 2nd ed, Rifai N, Warnick G R, Dominiczak M H, eds p. 609-623, AACC Press, Washington, D.C., 2000). This method is based on the idea that even when total LDL weight remains unchanged, the number of particles increases if LDL downsizes. Hence, the method is intended to indirectly measure small, dense LDL levels, but is not intended to directly measure one ingredient of a small, dense LDL.

Examples of a method for measuring small, dense LDL cholesterol include an ultracentrifugal method (e.g., Atherosclerosis, 48 p. 33-49, 1993: Atherosclerosis,106, p. 241-253, 1994), a method that involves quantification of peak area using a densitometer after electrophoresis (Atherosclerosis, 125, p. 231-42 1996), and a method that involves segmentation of LDL using HPLC and quantification of cholesterol in small, dense LDL fractions (Handbook of lipoprotein Testing, 2nd ed, Rifai N, Warnick G R, Dominiczak M H, eds p. 647-669, AACC Press Washington, D.C., 2000). Another example is a method that involves lipid staining of gels after agarose electrophoresis, performing computer analysis of the staining patterns, and thus quantifying lipoprotein (JP Patent Publication (Kokai) No. 2000-356641 A). FCHL diagnosis can be made by the above measurement methods via quantification of small, dense LDL cholesterol, however, these methods are poor in terms of ease and versatility and thus are used with difficulty for daily inspection sites. Moreover, when the measured values are used for computer analysis, the values are estimates found by calculation and thus problematic in terms of correctness.

The present inventors provide a method that comprises separating LDL into LDL of normal sizes and small, dense LDL using a separating agent comprising polyanion and divalent cation and then quantifying small, dense LDL cholesterol using a reagent for measurement of LDL cholesterol (clinical pathology, 25, p. 406-413, 2004). According to the present invention, the above method for measurement of small, dense LDL cholesterol can be appropriately used.

For example, sdLDL cholesterol can be measured according to the description of Clinical Pathology, 25, p. 406-413, 2004 as follows. When a serum or plasma is used as a sample and the sample is mixed with a separating agent comprising polyanion and divalent cation, in addition to LDL of normal sizes, VLDL, chylomicron, and the like form aggregates and the aggregates are removed from the reaction system by centrifugation, filtration, or the like. sdLDL and HDL that do not form aggregates remain in the reaction solution. Reagents that can be used for a two reagent system autoanalyzer based on the principle of a direct measurement method for LDL cholesterol are caused to act on the reaction solution. In a first reaction, cholesterol esterase and cholesterol oxidase are caused to act in the presence of a surfactant that acts on lipoprotein other than LDL to eliminate the thus generated hydrogen peroxide, so that HDL cholesterol alone in the reaction solution is eliminated. In the subsequent second reaction, sdLDL cholesterol in the sample is measured. For example, this can be performed by adding a surfactant that acts on at least LDL and then quantifying hydrogen peroxide generated by the action of cholesterol esterase and cholesterol oxidase added in the first step.

The method of the present invention is a method for detection and diagnosis of FCHL, however, is also a method for screening for FCHL. Moreover, the method is also a method for determination and evaluation of cardiovascular event probability such as arteriosclerosis that is caused by FCHL; that is, the risk of the occurrence of cardiovascular event. For example, the risk of a cardiovascular event probability can be determined to be low, moderate, or high based on the concentration of small, dense LDL cholesterol in a sample. Moreover, such event probability can be represented with numerical figures by relating the measured value to the frequency at which such an event occurs.

Furthermore, according to the method of the present invention, the risk of the occurrence of an event such as arteriosclerosis in the case of FCHL can be evaluated and determined, and whether or not arteriosclerosis in the case of FCHL is severe can be evaluated and determined.

When a quantified small, dense LDL cholesterol level is increased to a level higher than that of a normal subject not affected with FCHL (for example, when the mean small, dense LDL cholesterol level of normal subjects is 20 mg/dL, but a quantified serum small, dense LDL cholesterol level ranges from 30 mg/dL to 50 mg/dL, and preferably to higher than 40 mg/dL), the subject is determined to be affected with FCHL. Furthermore, the risk of the occurrence of arteriosclerotic disease in such subject is determined to be higher. However, the standard value for FCHL diagnosis is not limited to the above level, since the standard value may vary depending on ethnic differences, for example. Moreover, increases in severity of arteriosclerosis are suggested, as the measured small, dense LDL cholesterol levels of humans diagnosed to be affected with FCHL are found to increase to 45 mg/dL and 50 mg/dL. In such case, it can be determined that the risk of the onset of an arteriosclerotic disease such as cardiac infarction is high.

According to the method of the present invention for detection of FCHL using small, dense LDL cholesterol as a marker or the method of the same for evaluation and determination of the risk of arteriosclerotic disease, FCHL, which has been impossible to detect with the use of conventional lipid markers, can be detected and the risk of arteriosclerotic disease that has been impossible to evaluate and determine with the use of conventional lipid markers can be evaluated and determined. Specifically, in an FCHL patient, even when one, two, or all of TG, LDL-C, and HDL-C and preferably one of or both TG and LDL-C are at normal levels, the small, dense LDL cholesterol level may be higher than the normal level. Hence, the method of the present invention is a method for detection of FCHL, capable of detecting FCHL that has been impossible to detect with the use of conventional lipid markers such as TG, LDL-C, and HDL-C. Here, the term "normal level" refers to a level that is not significantly different statistically from the concentration of an analyte in a test sample collected from a subject clinically determined to be normal.

EXAMPLES

Hereafter, the present invention is described in greater detail with reference to the following examples, although the present invention is not limited thereto.

Example 1

Three hundred and sixty (360) male and female healthy normal subjects who had not developed arteriosclerotic disease and 9 subjects who had been confirmed to be affected with FCHL by examination of subjects or based on the family history were subjected to the measurement of small, dense LDL cholesterol. For measurement of small, dense LDL cholesterol, sdLDL-C "Seiken" (produced by Denka Seiken Co., Ltd.) was used.

FIG. 1 shows the result. As shown in FIG. 1, the small, dense LDL cholesterol level was clearly found to increase in the FCHL group compared with that in the healthy normal group. This result demonstrates that FCHL disease can be detected satisfactorily by quantification of small, dense LDL cholesterol.

Example 2

Various lipid parameters in samples obtained from the FCHL patient group used in Example 1 were compared. Reagents similar to those used in Example 1 were used for measurement of small, dense LDL cholesterol. Triglyceride, LDL-cholesterol, and HDL-cholesterol were measured by an enzyme method.

Table 1 shows the results. A subject is generally diagnosed to be affected with an arteriosclerotic disease if the level of lipid marker TG or LDL-C in a sample other than samples obtained from FCHL patients is high. As shown in Table 1, the levels of TG or LDL-C were found to be low in some samples obtained from FCHL patients. Small, dense LDL cholesterol levels were high in all cases. This indicates that small, dense LDL cholesterol can be a measurement marker for diagnosis of FCHL, which has superior specificity to those of conventional lipid markers.

TABLE 1

|   | Gender | Age | TG | LDL-C | HDL-C | sdLDL-C |
|---|---|---|---|---|---|---|
| 1 | M | 38 | 250 | 250 | 33 | 117.4 |
| 2 | M | 40 | 645 | 103 | 31 | 70.9 |
| 3 | M | 46 | 657 | 105 | 43 | 55.5 |
| 4 | M | 54 | 135 | 175 | 50 | 46.8 |
| 5 | M | 55 | 1334 | 85 | 54 | 49.8 |
| 6 | M | 63 | 1156 | 81 | 39 | 45.2 |
| 7 | M | 65 | 77 | 266 | 50 | 95.1 |
| 8 | F | 59 | 130 | 132 | 53 | 76.8 |
| 9 | F | 65 | 212 | 158 | 34 | 59.2 |

Unit: mg/dL
TG: Triglyceride; LDL-C: LDL cholesterol; HDL-C: HDL cholesterol; and sdLDL-C: small, dense LDL cholesterol

Example 3

Healthy normal subjects (1345 cases) without diabetes and coronary artery disease were subjected to small, dense LDL cholesterol measurement using sdLDL-C "Seiken" (produced by Denka Seiken Co., Ltd.).

Figure 2:
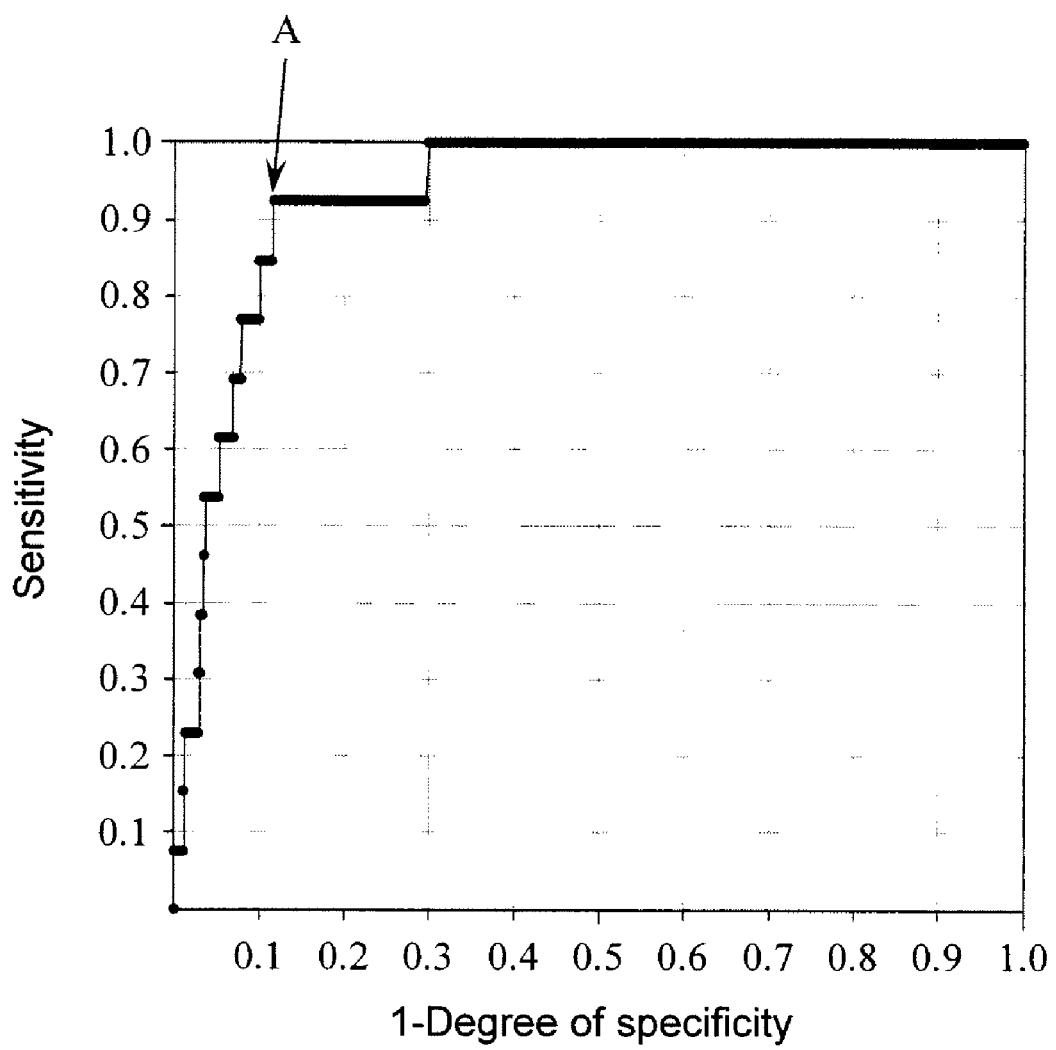
FIG. 2 shows an ROC curve when the small, dense LDL cholesterol levels for an FCHL group and a non-FCHL group were determined to be cut-off values.

Samples were specified and grouped if they were derived from FCHL patients or non-FCHL subjects based on family history (a factor for definition of FCHL) and their hyperlipidemia. Sensitivity and specificity were measured when the cut-off value of sdLDL-C was varied and then a receiver operating characteristic (ROC) curve was produced (FIG. 2).

As a result, when sdLDL-C on the upper left (point A) on the ROC curve was 40 mg/dL, the sensitivity was 92.3% and the specificity was 88.3%. This value with extremely high sensitivity and specificity was tentatively determined to be a cut-off value.

Example 4

A method for detection of FCHL using an sdLDL-C value of 40 mg/dL as a cut-off value, as found in Example 3, a method based on LDL sizes, which is an existing method for detection of FCHL, and a method based on the ratio of apoprotein B to LDL cholesterol were compared. The method based on LDL sizes is a method by which a result is found to be positive if LDL with a particle size of less than 25.5 nm is present. The method based on the ratio of apoprotein B to LDL cholesterol is a method by which a result is found to be positive in a case in which ApoB/LDL-C>1.0 (Guidelines for Diagnosis and Prevention of Arteriosclerotic Diseases 2002, ed., by Japan Atherosclerosis Society).

FIG. 3 shows the results. In FIG. 3A to FIG. 3D, the columns of confirmed diagnosis show the numbers of samples when the samples were specified and grouped if they were derived from FCHL patients or non-FCHL subjects based on family history (a factor for definition of FCHL) and their hyperlipidemia. "+" denotes the number of samples diagnosed with FCHL and "−" denotes the number of samples diagnosed with non-FCHL. In FIG. 3A, the columns of the present invention and sdLDL>40 mg/dL show the number of samples when the samples were specified and grouped if they were derived from FCHL patients or non-FCHL subjects by the method of the present invention using the sdLDL-C value as a cut-off value (40 mg·dL). In FIG. 3B, the columns of LDL size show the number of samples when the samples were specified and grouped if they were derived from FCHL patients or non-FCHL subjects by the method based on LDL size. In FIG. 3C, the columns of ApoB/LDL>1.0 show the number of samples when the samples were specified and grouped if they were derived from FCHL patients or non-FCHL subjects using the ratio of apoprotein B to LDL cholesterol as a cut-off value (10) and in FIG. 3D, the columns of the same show the number of samples when samples were specified and grouped if they were derived from FCHL patients or non-FCHL subjects using LDL size or the ratio of apoprotein B to LDL cholesterol as a cut-off value (10). "+" denotes the number of samples diagnosed with FCHL by each method. "−" denotes the number of samples not diagnosed with FCHL. As shown in FIG. 3A to FIG. 3D, the sensitivity and specificity of the method of the present invention, the method based on LDL sizes, the method using the ratio of apoprotein B to LDL cholesterol, and the method using LDL sizes or the ratio of apoprotein B to LDL cholesterol as a cut-off value (10) were 92.3% and 88.3%, 30.8% and 91.5%, 7.7% and 97.5%, and 30.8% and 90.6%, respectively. The thus obtained results demonstrate that the method of the present invention by which diagnosis is made using the sdLDL-C value is superior to the existing methods in terms of sensitivity and specificity.

Based on the results in Examples 3 and 4, it can be said that a subject is determined to be affected with FCHL when the sdLDL-C is 40 mg/dL, and the risk of arteriosclerotic disease is determined to be higher in such subject.

All publications, patents, and patent applications cited in the description are herein incorporated by reference in their entirety.

The invention claimed is:

1. A method for detection of familial combined hyperlipidemia, comprising, for a serum or plasma sample collected from a subject,
   (i) separating small, dense low density lipoprotein (LDL) from other LDLs or eliminating cholesterols other than small, dense LDL, and then
   (ii) measuring the concentration of small, dense LDL in the serum or plasma sample, wherein the subject having a small, dense LDL concentration of higher than a cutoff value of 40 mg/dL is diagnosed to have familial combined hyperlipidemia, and wherein the cutoff value is determined by producing a receiver operating characteristic (ROC) curve.

2. The method according to claim 1, comprising measuring the concentration of small, dense LDL in the sample collected from the subject, in which sample the triglyceride or LDL-cholesterol level is normal.

3. The method according to claim 1, wherein separation of small, dense LDL from other LDLs is achieved by performing reaction for LDL other than the small, dense LDL.

4. The method according to claim 1, wherein said concentration of small, dense LDL higher than 40 mg/dL is used as the sole indicator of familial combined hyperlipidemia.

5. A method for determination of the risk of the occurrence of arteriosclerotic disease in a subject with familial combined hyperlipidemia, comprising for a serum or plasma sample collected from the subject:
   (i) separating small, dense low density lipoprotein (LDL) from other LDLs or eliminating cholesterols other than small, dense LDL in the serum or plasma sample collected from the subject; and
   (ii) measuring the concentration of small, dense LDL in the serum or plasma sample, wherein the subject having a small, dense LDL concentration of higher than a cutoff value of 40 mg/dL is determined to have the risk of the occurrence of arteriosclerotic disease, wherein the cutoff value is determined by producing a receiver operating characteristic (ROC) curve.

6. The method according to claim 5, wherein separation of small, dense LDL from other LDLs is achieved by performing reaction for LDLs other than the small, dense LDL.

7. The method according to claim 5, wherein said concentration of small, dense LDL higher than 40 mg/dL is used as the sole indicator of determination of the risk of the occurrence of arteriosclerotic disease.

* * * * *